United States Patent [19]

Takematsu et al.

[11] Patent Number: 4,554,015

[45] Date of Patent: Nov. 19, 1985

[54] HERBICIDES

[75] Inventors: Tetsuo Takematsu; Makoto Konnai; Hideo Morinaka, all of Utsunomiya; Yuji Nonaka, Shinnanyo; Akira Nakanishi, Shinnanyo; Kenji Tsuzuki, Shinnanyo; Mitsuyuki Hashihama, Shinnanyo; Takeshi Uwotani, Shinnanyo, all of Japan

[73] Assignee: Toyo Soda Manufacturing Co., Ltd., Shinnanyo, Japan

[21] Appl. No.: 506,892

[22] Filed: Jun. 22, 1983

[30] Foreign Application Priority Data

Jun. 23, 1982 [JP] Japan ................................. 57-106737
Aug. 17, 1982 [JP] Japan ................................. 57-141712
Feb. 2, 1983 [JP] Japan ................................. 58-14596
Mar. 1, 1983 [JP] Japan ................................. 58-31836

[51] Int. Cl.$^4$ ........................................... A01N 37/00
[52] U.S. Cl. ..................................................... 71/100
[58] Field of Search ...................... 71/100; 260/455 A

[56] References Cited

U.S. PATENT DOCUMENTS 3,030,243  1/1966  D'Amico .............................. 71/100
3,509,200  4/1970  Elpern et al. ................... 260/455 A
3,855,263  12/1974  Melloni et al. ................. 260/455 A

FOREIGN PATENT DOCUMENTS 627322    5/1963  Belgium .
3018670  11/1981  Fed. Rep. of Germany .
49925     7/1973  Japan .

OTHER PUBLICATIONS

Noguchi et al, Yakugaku Zasshi, vol. 88, No. 3, pp. 335–343; 344–352 (1968); No. 4, pp. 465–472, (1968).

*Primary Examiner*—Catherine L. Mills
*Attorney, Agent, or Firm*—Oblon, Fisher, Spivak, McClelland & Maier

[57] ABSTRACT

Herbicides containing thiocarbamate derivatives represented by the general formula (I) as an active ingredient

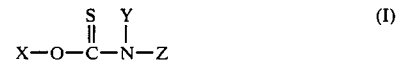

wherein
X is 5-indanyl, 5,6,7,8-tetrahydro-2-naphthyl, 1,4-methano-1,2,3,4-tetrahydro-6-naphthyl, 1,4-ethano-1,2,3,4-tetrahydro-6-naphthyl, or substituted phenyl,
Y is lower alkyl,
Z is naphthyl which is unsubstituted or phenyl which is unsubstituted or substituted.

5 Claims, No Drawings

HERBICIDES

DETAILED EXPLANATION OF THE INVENTION

The present invention concerns herbicides comprising thiocarbamate derivatives as an active ingredient.

Hitherto, it has been well-known that O-aryl N-arylthiocarbamate derivatives have antifungal activity and nematocidal activity as drugs and also that carbamate, thiolcarbamate and dithiocarbamate derivatives generally have herbicidal activity. For example, there is a description in Japanese unexamined patent publication No. 49925/1973 that some aryl N-arylcarbamate derivatives can be used as herbicides. However, it has been unknown that O-aryl N-arylthiocarbamate derivatives can be used as effective herbicides.

The present inventors have earnestly conducted an investigation to develop herbicides containing O-aryl N-arylthiocarbamate derivatives which exhibit sufficient herbicidal activity and high selectivity.

More especially, the present invention provides herbicides containing O-aryl N-arylthiocarbamate derivatives represented by the general formula (I) as an active ingredient (hereinafter referred to as the herbicides of the present invention)

  (I)

wherein
- X is 5-indanyl, 5,6,7,8-tetrahydro-2-naphthyl, 1,4-methano-1,2,3,4-tetrahydro-6-naphthyl, 1,4-ethano-1,2,3,4-tetrahydro-6-naphthyl, or substituted phenyl having one or two of the same or different substituents selected from the group of halogeno, lower alkyl, lower alkoxy, lower alkenyloxy, lower alkynyloxy, lower alkylthio, acyl, nitro, cyano, methylenedioxy, and trifluoromethyl,
- Y is lower alkyl,
- Z is naphthyl which is unsubstituted or phenyl which is unsubstituted or substituted by one or two of the same or different substituents selected from the group of halogeno, lower alkyl, lower alkoxy, lower alkylamino, trifluoromethyl, and fluorinated lower alkoxy.

The herbicides of the present invention show extremely excellent herbicidal activity against barnyard grass as well as many general weeds in the paddy field, and they are substantially harmless against transplanted rice plants. Therefore, these herbicides are suitable for use in the paddy field. In addition, the herbicides of the present invention were recognized to have an applicability to be used in the farmland from the observation that they showed excellent herbicidal selectivity between gramineous weeds and broadleaved crops in the soil treatment of the farmland.

Thiocarbamate derivatives represented by the general formula (I), an active ingredient of the herbicides of the present invention, can be prepared according to the following reaction equations (1) and (2)

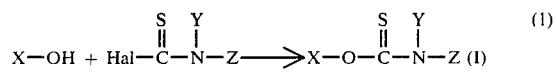  (1)

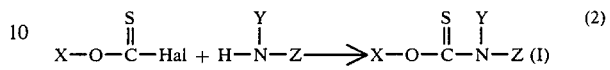  (2)

wherein
- X is 5-indanyl, 5,6,7,8-tetrahydro-2-naphthyl, 1,4-methano-1,2,3,4-tetrahydro-6-naphthyl, 1,4-ethano-1,2,3,4-tetrahydro-6-naphthyl, or substituted phenyl having one or two of the same or different substituents selected from the group of halogen, lower alkyl, lower alkoxy, lower alkenyloxy, lower alkynyloxy, lower alkylthio, acyl, nitro, cyano, methylenedioxy, and trifluoromethyl,
- Y is lower alkyl,
- Z is naphthyl which is unsubstituted or phenyl which is unsubstituted or substituted by one or two of the same or different substituents selected from the group of halogeno, lower alkyl, lower alkoy, lower alkylamino, trifluoromethyl, and fluorinated lower alkoxy,
- Hal is a halogen atom.

The above-stated reactions proceed in the presence of dehydrohalogenation agents and further in the presence or absence of reaction solvents usually at the reaction temperature ranging from 0° to 150° C. during the reaction time ranging from about few minutes to 48 hours.

As the dehydrohalogenation agents, alkali hydroxides such as sodium hydroxide, potassium hydroxide and the like; alkali earth hydroxides such as calcium hydroxide and the like; alkali carbonates such as sodium carbonate, potassium carbonate, sodium bicarbonate, potassium bicarbonate and the like; metal hydrides such as sodium hydride and the like; and tertiary amines such as triethylamine, N,N-dimethylaniline, pyridine and the like can be exemplified. The starting amine derivatives can be used as the dehydrohalogenation agents in the reaction shown by the equation (2).

As the reaction solvents, water; alcohols such as methanol, ethanol, isopropanol and the like; ketones such as acetone, methyl ethyl ketone and the like; aromatic hydrocarbons such as benzene, toluene, xylene, and the like; ethers such as ethyl ether, tetrahydrofuran, dioxane and the like; halogenated hydrocarbons such as chlorobenzene, chloroform, carbon tetrachloride, dichloroethane and the like; and polar solvents such as dimethylformamide, dimethylsulfoxide and the like can be used.

Typical example of thiocarbamate derivatives represented by the general formula (I) having number for an identification with those properties are shown hereinbelow.

| NO. | NAME OF THE THIOCARBAMATE DERIVATIVES AND THEIR PROPERTIES | |
|---|---|---|
| 1. | 0-5,6,7,8-Tetrahydro-2-naphthyl N—methyl-N—(3-methylphenyl)thiocarbamate | mp 51–54° C. |
| 2. | 0-5-Indanyl N—methyl-N—(3-methylphenyl)thiocarbamate | mp 97–99° C. |
| 3. | 0-1,4-Methano-1,2,3,4-tetrahydro-6-naphthyl N—methyl-N—(3-methylphenyl)thiocarbamate | mp 93.5–97° C. |
| 4. | 0-5-Indanyl N—methyl-N—phenylthiocarbamate | mp 88.5–90° C. |
| 5. | 0-5,6,7,8-Tetrahydro-2-naphthyl N—methyl-N—phenylthiocarbamate | mp 79–80° C. |
| 6. | 0-5-Indanyl N—methyl-N—(2-methylphenyl)thiocarbamate | mp 84–85.5° C. |
| 7. | 0-5,6,7,8-Tetrahydro-2-naphthyl N—methyl-N—(2-methylphenyl)thiocarbamate | mp 74.5–76° C. |

-continued

| NO. | NAME OF THE THIOCARBAMATE DERIVATIVES AND THEIR PROPERTIES | |
|---|---|---|
| 8. | O—5-Indanyl N—methyl-N—(4-methylphenyl)thiocarbamate | mp 66–68.5° C. |
| 9. | O—5,6,7,8-Tetrahydro-2-naphthyl N—methyl-N—(4-methylphenyl)thiocarbamate | mp 92.5–94° C. |
| 10. | O—5-Indanyl N—(2-ethylphenyl)-N—methylthiocarbamate | oil |
| 11. | O—5,6,7,8-Tetrahydro-2-naphthyl N—(2-ethylphenyl)-N—methylthiocarbamate | mp 63.5–65° C. |
| 12. | O—5-Indanyl N—(3-ethylphenyl)-N—methylthiocarbamate | mp 68–69° C. |
| 13. | O—5,6,7,8-Tetrahydro-2-naphthyl N—(3-ethylphenyl)-N—methylthiocarbamate | mp 48–49° C. |
| 14. | O—5-Indanyl N—(4-ethylphenyl)-N—methylthiocarbamate | oil |
| 15. | O—5,6,7,8-Tetrahydro-2-naphthyl N—(4-ethylphenyl)-N—methylthiocarbamate | mp 76.5–78.5° C. |
| 16. | O—5-Indanyl N—(2-fluorophenyl)-N—methylthiocarbamate | mp 105.5–108° C. |
| 17. | O—5,6,7,8-Tetrahydro-2-naphthyl N—(2-fluorophenyl)-N—methylthiocarbamate | mp 60.5–62° C. |
| 18. | O—5-Indanyl N—(3-fluorophenyl)-N—methylthiocarbamate | mp 100–101.5° C. |
| 19. | O—5,6,7,8-Tetrahydro-2-naphthyl N—(3-fluorophenyl)-N—methylthiocarbamate | mp 101–102.5° C. |
| 20. | O—5-Indanyl N—(4-fluorophenyl)-N—methylthiocarbamate | mp 82–84° C. |
| 21. | O—5,6,7,8-Tetrahydro-2-naphthyl N—(4-fluorophenyl)-N—methylthiocarbamate | mp 66–67° C. |
| 22. | O—5-Indanyl N—(2-chlorophenyl)-N—methylthiocarbamate | mp 98–100° C. |
| 23. | O—5,6,7,8-Tetrahydro-2-naphthyl N—(2-chlorophenyl)-N—methylthiocarbamate | mp 73–75° C. |
| 24. | O—5-Indanyl N—(3-chlorophenyl)-N—methylthiocarbamate | mp 121–122° C. |
| 25. | O—5,6,7,8-Tetrahydro-2-naphthyl N—(3-chlorophenyl)-N—methylthiocarbamate | mp 86–87° C. |
| 26. | O—5-Indanyl N—(4-chlorophenyl)-N—methylthiocarbamate | mp 108–109° C. |
| 27. | O—5,6,7,8-Tetrahydro-2-naphthyl N—(4-chlorophenyl)-N—methylthiocarbamate | mp 77–78.5° C. |
| 28. | O—5-Indanyl N—(2-bromophenyl)-N—methylthiocarbamate | mp 86–89° C. |
| 29. | O—5,6,7,8-Tetrahydro-2-naphthyl N—(2-bromophenyl)-N—methylthiocarbamate | mp 94–96° C. |
| 30. | O—5-Indanyl N—(3-bromophenyl)-N—methylthiocarbamate | mp 122.5–125° C. |
| 31. | O—5,6,7,8-Tetrahydro-2-naphthyl N—(3-bromophenyl)-N—methylthiocarbamate | mp 81.5–83° C. |
| 32. | O—5-Indanyl N—(2-methoxyphenyl)-N—methylthiocarbamate | mp 105–105.5° C. |
| 33. | O—5,6,7,8-Tetrahydro-2-naphthyl N—(2-methoxyphenyl)-N—methylthiocarbamate | oil |
| 34. | O—5-Indanyl N—(3-methoxyphenyl)-N—methylthiocarbamate | mp 89–90.5° C. |
| 35. | O—5,6,7,8-Tetrahydro-2-naphthyl N—(3-methoxyphenyl)-N—methylthiocarbamate | mp 88–88.5° C. |
| 36. | O—5,6,7,8-Tetrahydro-2-naphthyl N—(4-methoxyphenyl)-N—methylthiocarbamate | mp 92–93.5° C. |
| 37. | O—5-Indanyl N—(3-trifluoromethylphenyl)-N—methylthiocarbamate | mp 102.5–104° C. |
| 38. | O—5-Indanyl N—methyl-N—(2,3-dimethylphenyl)thiocarbamate | mp 118–119.5° C. |
| 39. | O—5,6,7,8-Tetrahydro-2-naphthyl N—methyl-N—(2,3-dimethylphenyl)thiocarbamate | mp 98.5–100° C. |
| 40. | O—5-Indanyl N—methyl-N—(2,4-dimethylphenyl)thiocarbamate | mp 79–80° C. |
| 41. | O—5,6,7,8-Tetrahydro-2-naphthyl N—methyl-N—(2,4-dimethylphenyl)thiocarbamate | mp 59–62° C. |
| 42. | O—5-Indanyl N—methyl-N—(2,5-dimethylphenyl)thiocarbamate | mp 141–144° C. |
| 43. | O—5,6,7,8-Tetrahydro-2-naphthyl N—methyl-N—(2,5-dimethylphenyl)thiocarbamate | mp 107–109.5° C. |
| 44. | O—5-Indanyl N—methyl-N—(3,4-dimethylphenyl)thiocarbamate | mp 112–113.5° C. |
| 45. | O—5,6,7,8-Tetrahydro-2-naphthyl N—methyl-N—(3,4-dimethylphenyl)thiocarbamate | mp 72–74° C. |
| 46. | O—5-Indanyl N—methyl-N—(3,5-dimethylphenyl)thiocarbamate | mp 162–165° C. |
| 47. | O—5,6,7,8-Tetrahydro-2-naphthyl N—methyl-N—(3,5-dimethylphenyl)thiocarbamate | mp 111–113° C. |
| 48. | O—5-Indanyl N—(3-chloro-2-methylphenyl)-N—methylthiocarbamate | mp 104–106.5° C. |
| 49. | O—5,6,7,8-Tetrahydro-2-naphthyl N—(3-chloro-2-methylphenyl)-N—methylthiocarbamate | mp 104.5–106° C. |
| 50. | O—5-Indanyl N—(3-chloro-4-methylphenyl)-N—methylthiocarbamate | mp 106–107° C. |
| 51. | O—5,6,7,8-Tetrahydro-2-naphthyl N—(3-chloro-4-methylphenyl)-N—methylthiocarbamate | mp 81.5–83° C. |
| 52. | O—5-Indanyl N—(5-chloro-2-methoxyphenyl)-N—methylthiocarbamate | mp 152.5–154.5° C. |
| 53. | O—5,6,7,8-Tetrahydro-2-naphthyl N—(5-chloro-2-methoxyphenyl)-N—methylthiocarbamate | mp 133.5–134.5° C. |
| 54. | O—5-Indanyl N—(3-methoxy-4-methylphenyl)-N—methylthiocarbamate | mp 96.5–97.5° C. |
| 55. | O—5,6,7,8-Tetrahydro-2-naphthyl N—(3-methoxy-4-methylphenyl)-N—methylthiocarbamate | mp 78–79.5° C. |
| 56. | O—5-Indanyl N—(3,4-dimethoxyphenyl)-N—methylthiocarbamate | mp 159–161° C. |
| 57. | O—5,6,7,8-Tetrahydro-2-naphthyl N—(3,4-dimethoxyphenyl)-N—methylthiocarbamate | mp 137.5–138.5° C. |
| 58. | O—5-Indanyl N—(3,4-dichlorophenyl)-N—methylthiocarbamate | mp 135–136° C. |
| 59. | O—5,6,7,8-Tetrahydro-2-naphthyl N—(3,4-dichlorophenyl)-N—methylthiocarbamate | mp 103–104° C. |
| 60. | O—5-Indanyl N—methyl-N—(1-naphthyl)thiocarbamate | mp 138–140.5° C. |
| 61. | O—3-tert-Butylphenyl N—methyl-N—(3-methylphenyl)thiocarbamate | mp 62–63.5° C. |
| 62. | O—4-tert-Butylphenyl N—methyl-N—(3-methylphenyl)thiocarbamate | mp 104–105° C. |
| 63. | O—3,4-Dimethylphenyl N—methyl-N—(3-methylphenyl)thiocarbamate | mp 82.5–83.5° C. |
| 64. | O—4-tert-Butylphenyl N—(3-methoxyphenyl)-N—methylthiocarbamate | mp 88–89° C. |
| 65. | O—4-tert-Butylphenyl N—(3-chlorophenyl)-N—methylthiocarbamate | mp 89–92° C. |
| 66. | O—4-tert-Butylphenyl N—(3,4-dichlorophenyl)-N—methylthiocarbamate | mp 108–109° C. |
| 67. | O—4-Methylphenyl N—methyl-N—(3-methylphenyl)thiocarbamate | mp 62–63° C. |
| 68. | O—4-Ethylphenyl N—methyl-N—(3-methylphenyl)thiocarbamate | oil |
| 69. | O—4-Isopropylphenyl N—methyl-N—(3-methylphenyl)thiocarbamate | mp 76.5–77° C. |
| 70. | O—4-sec-Butylphenyl N—methyl-N—(3-methylphenyl)thiocarbamate | mp 59–61° C. |
| 71. | O—4-tert-Pentylphenyl N—methyl-N—(3-methylphenyl)thiocarbamate | mp 87–88.5° C. |
| 72. | O—4-tert-Butylphenyl N—methyl-N—phenylthiocarbamate | mp 144.5–146° C. |
| 73. | O—4-tert-Butylphenyl N—methyl-N—(2-methylphenyl)thiocarbamate | mp 111–112° C. |
| 74. | O—4-tert-Butylphenyl N—methyl-N—(4-methylphenyl)thiocarbamate | mp 146.5–148° C. |
| 75. | O—4-tert-Butylphenyl N—(3-ethylphenyl)-N—methylthiocarbamate | mp 49.5–51.5° C. |
| 76. | O—4-tert-Butylphenyl N—(2-fluorophenyl)-N—methylthiocarbamate | mp 142–143° C. |
| 77. | O—4-tert-Butylphenyl N—(3-fluorophenyl)-N—methylthiocarbamate | mp 137.5–138.5° C. |
| 78. | O—4-tert-Butylphenyl N—(4-fluorophenyl)-N—methylthiocarbamate | mp 123–124.5° C. |
| 79. | O—4-tert-Butylphenyl N—(2-chlorophenyl)-N—methylthiocarbamate | mp 107.5–108.5° C. |
| 80. | O—4-tert-Butylphenyl N—(4-chlorophenyl)-N—methylthiocarbamate | mp 159–160.5° C. |
| 81. | O—4-tert-Butylphenyl N—(3-bromophenyl)-N—methylthiocarbamate | mp 70–71.5° C. |
| 82. | O—4-tert-Butylphenyl N—(2-methoxyphenyl)-N—methylthiocarbamate | mp 112–114° C. |
| 83. | O—4-tert-Butylphenyl N—(3-trifluoromethylphenyl)-N—methylthiocarbamate | mp 54–55° C. |
| 84. | O—4-tert-Butylphenyl N—methyl-N—(3,4-dimethylphenyl)thiocarbamate | mp 115.5–117° C. |
| 85. | O—4-tert-Butylphenyl N—methyl-N—(3,5-dimethylphenyl)thiocarbamate | mp 97–98.5° C. |
| 86. | O—4-tert-Butylphenyl N—(3-chloro-4-methylphenyl)-N—methylthiocarbamate | mp 104–106° C. |
| 87. | O—4-tert-Butylphenyl N—(3-methoxy-4-methylphenyl)-N—methylthiocarbamate | mp 113.5–114.5° C. |
| 88. | O—4-tert-Butylphenyl N—methyl-N—(1-naphthyl)thiocarbamate | mp 107–108° C. |

-continued

| NO. | NAME OF THE THIOCARBAMATE DERIVATIVES AND THEIR PROPERTIES | |
|---|---|---|
| 89. | O-4-tert-Pentylphenyl N—(3-methoxyphenyl)-N—methylthiocarbamate | mp 59–61° C. |
| 90. | O-4-Methoxyphenyl N—methyl-N—(3-methylphenyl)thiocarbamate | mp 94–95° C. |
| 91. | O-4-Butoxyphenyl N—methyl-N—(3-methylphenyl)thiocarbamate | oil |
| 92. | O-1,4-Ethano-1,2,3,4-tetrahydro-6-naphthyl N—methyl-N—(3-methylphenyl)thiocarbamate | mp 110–112° C. |
| 93. | O-3-tert-Butylphenyl N—(3-methoxyphenyl)-N—methylthiocarbamate | mp 64–65° C. |
| 94. | O-4-Butylphenyl N—methyl-N—(3-methylphenyl)thiocarbamate | oil |
| 95. | O-4-Isopropylphenyl N—(3-methoxyphenyl)-N—methylthiocarbamate | mp 51–53.5° C. |
| 96. | O-4-sec-Butylphenyl N—(3-methoxyphenyl)-N—methylthiocarbamate | oil |
| 97. | O-4-Isopropylphenyl N—methyl-N—phenylthiocarbamate | mp 87–88° C. |
| 98. | O-3-tert-Butylphenyl N—methyl-N—phenylthiocarbamate | mp 78.5–79° C. |
| 99. | O-3-tert-Butylphenyl N—methyl-N—(2-methylphenyl)thiocarbamate | mp 98.5–99.5° C. |
| 100. | O-3-tert-Butylphenyl N—methyl-N—(4-methylphenyl)thiocarbamate | mp 80.5–81.5° C. |
| 101. | O-3-tert-Butylphenyl N—(2-fluorophenyl)-N—methylthiocarbamate | mp 79.5–81° C. |
| 102. | O-3-tert-Butylphenyl N—(3-fluorophenyl)-N—methylthiocarbamate | mp 75–77° C. |
| 103. | O-3-tert-Butylphenyl N—(4-fluorophenyl)-N—methylthiocarbamate | oil |
| 104. | O-3-tert-Butylphenyl N—(3-bromophenyl)-N—methylthiocarbamate | mp 84–86° C. |
| 105. | O-3-tert-Butylphenyl N—(3-trifluoromethylphenyl)-N—methylthiocarbamate | oil |
| 106. | O-3-tert-Butylphenyl N—methyl-N—(3,4-dimethylphenyl)thiocarbamate | mp 115–116° C. |
| 107. | O-3-tert-Butylphenyl N—methyl-N—(3,5-dimethylphenyl)thiocarbamate | mp 70–72° C. |
| 108. | O-3-tert-Butylphenyl N—(3-chloro-4-methylphenyl)-N—methylthiocarbamate | mp 89–90° C. |
| 109. | O-3-tert-Butylphenyl N—(3-methoxy-4-methylphenyl)-N—methylthiocarbamate | oil |
| 110. | O-3-tert-Butylphenyl N—(3-ethylphenyl)-N—methylthiocarbamate | mp 84.5–85.5° C. |
| 111. | O-5-Isopropyl-2-methylphenyl N—methyl-N—phenylthiocarbamate | oil |
| 112. | O-5-Isopropyl-2-methylphenyl N—methyl-N—(3-methylphenyl)thiocarbamate | oil |
| 113. | O-5-Isopropyl-2-methylphenyl N—(3-methoxyphenyl)-N—methylthiocarbamate | oil |
| 114. | O-3-Methylphenyl N—methyl-N—(3-methylphenyl)thiocarbamate | oil |
| 115. | O-3-Ethylphenyl N—methyl-N—(3-methylphenyl)thiocarbamate | oil |
| 116. | O-3-Isopropylphenyl N—methyl-N—(3-methylphenyl)thiocarbamate | mp 48–49.5° C. |
| 117. | O-3-tert-Butylphenyl N—(2-chlorophenyl)-N—methylthiocarbamate | mp 85.5–86.5° C. |
| 118. | O-3-tert-Butylphenyl N—(3-chlorophenyl)-N—methylthiocarbamate | oil |
| 119. | O-3-tert-Butylphenyl N—(4-chlorophenyl)-N—methylthiocarbamate | oil |
| 120. | O-3-tert-Butylphenyl N—(2-methoxyphenyl)-N—methylthiocarbamate | mp 88.5–90° C. |
| 121. | O-3-tert-Butylphenyl N—(4-methoxyphenyl)-N—methylthiocarbamate | oil |
| 122. | O-3-tert-Butylphenyl N—(3,4-dichlorophenyl)-N—methylthiocarbamate | oil |
| 123. | O-3-tert-Butylphenyl N—ethyl-N—phenylthiocarbamate | oil |
| 124. | O-4-Ethyl-3-methylphenyl N—methyl-N—(3-methylphenyl)thiocarbamate | oil |
| 125. | O-4-Cyanophenyl N—methyl-N—phenylthiocarbamate | oil |
| 126. | O-3-Ethoxyphenyl N—(3-methoxyphenyl)-N—methylthiocarbamate | mp 81.5–82.5° C. |
| 127. | O-2-Chlorophenyl N—methyl-N—(3-methylphenyl)thiocarbamate | oil |
| 128. | O-3-Chlorophenyl N—methyl-N—phenylthiocarbamate | oil |
| 129. | O-4-Chlorophenyl N—(3-methoxyphenyl)-N—methylthiocarbamate | mp 91–92° C. |
| 130. | O-3-Bromophenyl N—methyl-N—(3-methylphenyl)thiocarbamate | mp 72–73° C. |
| 131. | O-4-Bromophenyl N—(3-methoxyphenyl)-N—methylthiocarbamate | mp 104–105° C. |
| 132. | O-3-Trifluoromethylphenyl N—methyl-N—(3-methylphenyl)thiocarbamate | mp 86–87° C. |
| 133. | O-4-Nitrophenyl N—(3-methoxyphenyl)-N—methylthiocarbamate | mp 81.5–82.5° C. |
| 134. | O-4-Acetylphenyl N—(3-methoxyphenyl)-N—methylthiocarbamate | mp 90.5–91.5° C. |
| 135. | O-4-Methylthiophenyl N—methyl-N—phenylthiocarbamate | mp 90–91° C. |
| 136. | O-3,4-Methylenedioxyphenyl N—methyl-N—phenylthiocarbamate | mp 106.5–107.5° C. |
| 137. | O-4-Chloro-3-methylphenyl N—methyl-N—phenylthiocarbamate | mp 79–80° C. |
| 138. | O-4-Chloro-3-methylphenyl N—methyl-N—(2-methylphenyl)thiocarbamate | mp 102–103.5° C. |
| 139. | O-4-Chloro-3-methylphenyl N—methyl-N—(3-methylphenyl)thiocarbamate | mp 100.5–102° C. |
| 140. | O-4-Chloro-3-methylphenyl N—methyl-N—(4-methylphenyl)thiocarbamate | mp 67–68° C. |
| 141. | O-4-Chloro-3-methylphenyl N—(3-ethylphenyl)-N—methylthiocarbamate | oil |
| 142. | O-4-Chloro-3-methylphenyl N—(3-fluorophenyl)-N—methylthiocarbamate | mp 104.5–106° C. |
| 143. | O-4-Chloro-3-methylphenyl N—(2-chlorophenyl)-N—methylthiocarbamate | mp 104–105° C. |
| 144. | O-4-Chloro-3-methylphenyl N—(3-chlorophenyl)-N—methylthiocarbamate | mp 104–105° C. |
| 145. | O-4-Chloro-3-methylphenyl N—(4-chlorophenyl)-N—methylthiocarbamate | mp 70–72° C. |
| 146. | O-4-Chloro-3-methylphenyl N—(3-bromophenyl)-N—methylthiocarbamate | mp 124–126° C. |
| 147. | O-4-Chloro-3-methylphenyl N—(3-trifluoromethylphenyl)-N—methylthiocarbamate | mp 97.5–99° C. |
| 148. | O-4-Chloro-3-methylphenyl N—(3-methoxyphenyl)-N—methylthiocarbamate | mp 111–113° C. |
| 149. | O-4-Chloro-3-methylphenyl N—(3,4-dichlorophenyl)-N—methylthiocarbamate | mp 86.5–88° C. |
| 150. | O-4-Chloro-3-methylphenyl N—methyl-N—(3,4-dimethylphenyl)thiocarbamate | mp 121.5–123° C. |
| 151. | O-4-Chloro-3-methylphenyl N—methyl-N—(3,5-dimethylphenyl)thiocarbamate | mp 118–120° C. |
| 152. | O-4-Chloro-3-methylphenyl N—(3-chloro-4-methylphenyl)-N—methylthiocarbamate | mp 91–93° C. |
| 153. | O-4-Chloro-3-methylphenyl N—ethyl-N—phenylthiocarbamate | mp 98–100° C. |
| 154. | O-3-Methyl-4-methylthiophenyl N—methyl-N—(3-methylphenyl)thiocarbamate | mp 100–102° C. |
| 155. | O-3-Methyl-4-nitrophenyl N—methyl-N—(3-methylphenyl)thiocarbamate | mp 91–93° C. |
| 156. | O-4-Chloro-3-methoxyphenyl N—methyl-N—(3-methylphenyl)thiocarbamate | mp 80–81.5° C. |
| 157. | O-3-Allyloxy-4-chlorophenyl N—methyl-N—(3-methylphenyl)thiocarbamate | mp 69–70.5° C. |
| 158. | O-4-Chloro-3-(2-propynyloxy)phenyl N—methyl-N—(3-methylphenyl)thiocarbamate | oil |
| 159. | O-4-Methylthiophenyl N—(3-methoxyphenyl)-N—methylthiocarbamate | mp 72–73.5° C. |
| 160. | O-5,6,7,8-Tetrahydro-2-naphthyl N—(4-trifluoromethoxyphenyl)-N—methylthiocarbamate | mp 86–88° C. |
| 161. | O-5,6,7,8-Tetrahydro-2-naphthyl N—[4-(1,1,2,2-tetrafluoroethoxy)phenyl]-N—methylthiocarbamate | mp 78–80.5° C. |
| 162. | O-3-Isopropylphenyl N—methyl-N—phenylthiocarbamate | oil |
| 163. | O-3-Isopropylphenyl N—(3-methoxyphenyl)-N—methylthiocarbamate | mp 60–61° C. |
| 164. | O-3-Isopropylphenyl N—(3-chlorophenyl)-N—methylthiocarbamate | oil |
| 165. | O-5,6,7,8-Tetrahydro-2-naphthyl N—methyl-N—(3-dimethylaminophenyl)thiocarbamate | oil |
| 166. | O-5-Indanyl N—methyl-N—(3-dimethylaminophenyl)thiocarbamate | mp 85.5–87.5° C. |
| 167. | O-4-tert-Butylphenyl N—methyl-N—(3-dimethylaminophenyl)thiocarbamate | mp 107–109° C. |
| 168. | O-1,4-Methano-1,2,3,4-tetrahydro-6-naphthyl N—methyl-N—(3-dimethylaminophenyl)-thiocarbamate | mp 97–98.5° C. |
| 169. | O-3-tert-Butylphenyl N—methyl-N—(3-dimethylaminophenyl)thiocarbamate | mp 76–77° C. |

-continued

| NO. | NAME OF THE THIOCARBAMATE DERIVATIVES AND THEIR PROPERTIES | |
|---|---|---|
| 170. | 0-4-Trifluoromethylphenyl N—methyl-N—(3-methylphenyl)thiocarbamate | mp 81.5–82.5° C. |
| 171. | 0-4-Trifluoromethylphenyl N—(3-methoxyphenyl)-N—methylthiocarbamate | mp 51–51.5° C. |
| 172. | 0-4-Bromo-3-methylphenyl N—methyl-N—(3-methylphenyl)thiocarbamate | mp 82–84° C. |
| 173. | 0-4-Bromo-3-methylphenyl N—(3-methoxyphenyl)-N—methylthiocarbamate | oil |
| 174. | 0-3-Chloro-4-methylphenyl N—(3-methoxyphenyl)-N—methylthiocarbamate | mp 82–83° C. |

In order to use the herbicides of the present invention, proper amount of one or more than one of the thiocarbamate derivatives represented by the above-stated general formula (I) is incorporated with inert carriers to use as usual agricultural chemicals like water dispersible powder, emulsifiable concentrate, granules, dust and so on.

As solid carriers, talc, clay, diatomaceous earth, bentonite, kaoline, Japanese acid clay, white carbon, pumice powder and the like are exemplified. As liquid carriers, water, alcohol, benzene, toluene, xylene, kerosine, cyclohexane, cyclohexanone, isophorone, Butyl Cellosolve, benzyl acetate, dimethylformamide, mineral oil and the like are used.

Furthermore, surface-active agents and stabilizers can be added when they are required. In addition, the herbicides of the present invention can be applied after incorporating them with other agricultural chemicals used in the same field, for example, insecticides, fungicides, herbicides, plant growth regulators or fertilizers. Especially, there will be occasions for the herbicides of the present invention that it is proper to be mixed with other herbicides for the purpose of reducing labor for spreading or for the purpose of extending the spectrum of weed species to be effectively prevented.

As herbicides to be added, triazine herbicides such as Atrazine, Simazine, Simetryn, Prometryn and the like; carbamate herbicides such as Asulam, Benthiocarb, Molinate and the like; urea herbicides such as Linuron, Dymrone and the like; phenoxy-series herbicides such as 2,4-D, MCP, MCPB, Naproanilide and the like; diphenyl ether herbicides such as Nitrofen, Chlornitrofen, Chlomethoxynil and the like; heterocyclic-series herbicides such as Oxadiazon, Pyrazolate, Bentazon and the like; and amide herbicides such as Alachlor, Butachlor, Propanil and the like can be exemplified. It is possible to provide mixtures of the herbicides of the present invention by being skillfully combined with one or more than one of the herbicides described above to be effctive to many weed species.

Examples of the formulation to prepare the herbicides of the present invention containing the thiocarbamate derivatives represented by the above-mentioned general formula (I) are explained herein-below. In the Examples, the term "parts" means parts by weight.

EXAMPLE 1
[Water Dispersible Powder]

A mixture of the compound No. 14 (10 parts), Zeeklite (Trade Name, manufactured by Kunimine Kogyo Co., Ltd. 87.3 parts) used as the carrier material, Neopelex (Trade Name, manufactured by Kao Atlas Co., Ltd., 1.35 parts); and Solpol 800A (Trade Name, manufactured by Toho Kogyo Co., Ltd., 1.35 parts) was pulverized to give 10% water dispersible powder.

EXAMPLE 2
[Emulsifiable Concentrate]

A mixture of the compound No. 15 (25 parts) and Solpol 800A (10 parts) was dissolved in 65 parts of benzene to give 25% emulsifiable concentrate.

EXAMPLE 3
[Granules]

A mixture of the compound No. 24 (10 parts), 50 parts of bentonite, 35 parts of Kunilite (Trade Name, manufactured by Kokuho Kogyo Co., Ltd.) and 5 parts of Solpol 800A used as the surface-active agent was pulverized. After 10 parts of water was added, the mixture was kneaded to give a homogeneous mixture and then the mixture was extruded through sieving perforations having a diameter of 0.7 mm and dried. The product was cut off to give 10% granules having length of 1-2 mm.

The herbicides of the present invention do not show any phytotoxicity against many useful crops like rice, soybean, cotton and the like but have excellent herbicidal activity against various weeds. More particularly, as to the herbicidal action of the presently invented herbicides, characteristic features are that these herbicides kill weeds, or inhibit the growth, or suppress the growth considerably to result in a failure of growth competition against crops.

Application amount of the herbicides of the present invention is generally in the range of 10 to 1000 g/10 ares, preferably 50 to 500 g/10 ares as an active ingredient although it differs depending upon the place applied, the application time, the application methods, and weeds to be avoided.

The herbicides of the present invention were found to have outstanding herbicidal activity against barnyard grass as well as many weeds such as umbrella plant, monochoria, tooth cup, bulrush and so on in the use of 50–500 g/10 ares as an active ingredient, especially under submerged paddy field condition. In addition, the herbicides of the present invention are highly safe to young seedling of rice plants and no affection has been observed even in the application amount of 1000 g/10 ares as an active ingredient. Therefore, the herbicides of the present invention have extremely excellent characteristics to be used for paddy field. Furthermore, the application period can be considerably extended since some of the herbicides of the present invention have good herbicidal activity against barnyard grass even in a growth period (1- to 3-leaf stage). That is to say, it was shown that these herbicides have high applicability as soil-applied agents in a cultivation of transplanted rice plants at the primary to medium stage and immediately after flooding in a cultivation of dry-seeded rice.

Surprisingly, it was also shown that some of the herbicides of the present invention have high applicability to be used in farmland because those herbicides, when they are used as soil-applied agents after the seeding of general broadleaved crops like soybean, effectively prevent gramineous weeds such as barnyard grass, crab grass, and foxtail without any phytotoxicity to crops.

The herbicidal effects of the presently invented herbicides are explained in the below-stated Examples.

EXAMPLE 4

[Test for the Herbicidal Effects Under Submerged Conditions (1)]

Paddy field soil was charged in porcelain pots having a diameter of 9 cm, and then water was added. After the soil was tilled, weed seeds were sown on the surface of the soil and two bunches of rice plants (variety: Nihonbare) being in 2-leaf stage were transplanted in 1 cm depth. The pots were flooded to give water depth of 2 cm on the next day and predetermined amount of water dispersible powder of the herbicides of the present invention, which was dispersed in 10 ml of water, was added dropwise onto the surface of water in every pots for the treatment. Then they were settled in a greenhouse and received water in proper time intervals. After 3 weeks from the treatment with chemicals, the herbicidal effects as well as the influence against the rice plants were examined. Evaluation is expressed by 6 stage system, details of which are shown below. The obtained results are shown in Table 1.

| Ex-pression | Phytotoxicity against rice plants | Herbicidal effects |
| --- | --- | --- |
| 5 | Killed | 100% Prevention (Amount of residual weeds: 0%) |
| 4 | Considerably injured | 80% Prevention (Amount of residual weeds: 20%) |
| 3 | Substantially injured | 60% Prevention (Amount of residual weeds: 40%) |
| 2 | A little injured | 40% Prevention (Amount of residual weeds: 60%) |
| 1 | Slightly injured | 20% Prevention (Amount of residual weeds: 80%) |
| 0 | No injured | 0% Prevention (Amount of residual weeds: 100%) |

TABLE 1

| Compound No. | Dose (g/10 ares) | Phytotoxicity against rice plant | Barnyard grass | Umbrella plant | Bulrush | Monochoria | Tooth cup |
| --- | --- | --- | --- | --- | --- | --- | --- |
| 1 | 125 | 0 | 5 | 5 | 4 | 5 | 5 |
|  | 250 | 0 | 5 | 5 | 5 | 5 | 5 |
|  | 500 | 0 | 5 | 5 | 5 | 5 | 5 |
|  | 1000 | 0 | 5 | 5 | 5 | 5 | 5 |
| 3 | 125 | 0 | 5 | 5 | 5 | 5 | 5 |
|  | 250 | 0 | 5 | 5 | 5 | 5 | 5 |
|  | 500 | 0 | 5 | 5 | 5 | 5 | 5 |
|  | 1000 | 0 | 5 | 5 | 5 | 5 | 5 |
| 4 | 125 | 0 | 5 | 5 | 4 | 5 | 5 |
|  | 250 | 0 | 5 | 5 | 5 | 5 | 5 |
|  | 500 | 0 | 5 | 5 | 5 | 5 | 5 |
|  | 1000 | 0 | 5 | 5 | 5 | 5 | 5 |
| 7 | 125 | 0 | 5 | 5 | 4 | 5 | 4 |
|  | 250 | 0 | 5 | 5 | 5 | 5 | 5 |
|  | 500 | 0 | 5 | 5 | 5 | 5 | 5 |
|  | 1000 | 0 | 5 | 5 | 5 | 5 | 5 |
| 9 | 125 | 0 | 5 | 5 | 3 | 5 | 5 |
|  | 250 | 0 | 5 | 5 | 4 | 5 | 5 |
|  | 500 | 0 | 5 | 5 | 5 | 5 | 5 |
|  | 1000 | 0 | 5 | 5 | 5 | 5 | 5 |
| 10 | 125 | 0 | 5 | 5 | 2 | 5 | 5 |
|  | 250 | 0 | 5 | 5 | 3 | 5 | 5 |
|  | 500 | 0 | 5 | 5 | 4 | 5 | 5 |
|  | 1000 | 0 | 5 | 5 | 4 | 5 | 5 |
| 16 | 125 | 0 | 5 | 5 | 4 | 5 | 5 |
|  | 250 | 0 | 5 | 5 | 5 | 5 | 5 |
|  | 500 | 0 | 5 | 5 | 5 | 5 | 5 |
|  | 1000 | 0 | 5 | 5 | 5 | 5 | 5 |
| 19 | 125 | 0 | 5 | 5 | 2 | 5 | 5 |
|  | 250 | 0 | 5 | 5 | 3 | 5 | 5 |
|  | 500 | 0 | 5 | 5 | 3 | 5 | 5 |
|  | 1000 | 0 | 5 | 5 | 4 | 5 | 5 |
| 21 | 125 | 0 | 5 | 5 | 4 | 5 | 5 |
|  | 250 | 0 | 5 | 5 | 5 | 5 | 5 |
|  | 500 | 0 | 5 | 5 | 5 | 5 | 5 |
|  | 1000 | 0 | 5 | 5 | 5 | 5 | 5 |
| 24 | 125 | 0 | 5 | 5 | 3 | 5 | 5 |
|  | 250 | 0 | 5 | 5 | 4 | 5 | 5 |
|  | 500 | 0 | 5 | 5 | 5 | 5 | 5 |
|  | 1000 | 0 | 5 | 5 | 5 | 5 | 5 |
| 27 | 125 | 0 | 5 | 5 | 2 | 4 | 4 |
|  | 250 | 0 | 5 | 5 | 3 | 5 | 5 |
|  | 500 | 0 | 5 | 5 | 4 | 5 | 5 |
|  | 1000 | 0 | 5 | 5 | 4 | 5 | 5 |
| 31 | 125 | 0 | 5 | 5 | 4 | 5 | 5 |
|  | 250 | 0 | 5 | 5 | 4 | 5 | 5 |
|  | 500 | 0 | 5 | 5 | 5 | 5 | 5 |
|  | 1000 | 0 | 5 | 5 | 5 | 5 | 5 |
| 33 | 125 | 0 | 5 | 5 | 4 | 5 | 5 |
|  | 250 | 0 | 5 | 5 | 5 | 5 | 5 |
|  | 500 | 0 | 5 | 5 | 5 | 5 | 5 |
|  | 1000 | 0 | 5 | 5 | 5 | 5 | 5 |
| 35 | 125 | 0 | 5 | 5 | 3 | 5 | 5 |
|  | 250 | 0 | 5 | 5 | 3 | 5 | 5 |
|  | 500 | 0 | 5 | 5 | 4 | 5 | 5 |

TABLE 1-continued

| Compound No. | Dose (g/10 ares) | Phytotoxicity against rice plant | Herbicidal effects ||||
|---|---|---|---|---|---|---|---|
| | | | Barnyard grass | Umbrella plant | Bulrush | Monochoria | Tooth cup |
| | 1000 | 0 | 5 | 5 | 4 | 5 | 5 |
| 44 | 125 | 0 | 5 | 5 | 1 | 5 | 5 |
| | 250 | 0 | 5 | 5 | 2 | 5 | 5 |
| | 500 | 0 | 5 | 5 | 3 | 5 | 5 |
| | 1000 | 0 | 5 | 5 | 3 | 5 | 5 |
| 48 | 125 | 0 | 5 | 5 | 0 | 5 | 5 |
| | 250 | 0 | 5 | 5 | 0 | 5 | 5 |
| | 500 | 0 | 5 | 5 | 1 | 5 | 5 |
| | 1000 | 0 | 5 | 5 | 2 | 5 | 5 |
| 51 | 125 | 0 | 5 | 5 | 1 | 5 | 5 |
| | 250 | 0 | 5 | 5 | 1 | 5 | 5 |
| | 500 | 0 | 5 | 5 | 2 | 5 | 5 |
| | 1000 | 0 | 5 | 5 | 2 | 5 | 5 |
| 55 | 125 | 0 | 5 | 5 | 2 | 5 | 5 |
| | 250 | 0 | 5 | 5 | 3 | 5 | 5 |
| | 500 | 0 | 5 | 5 | 4 | 5 | 5 |
| | 1000 | 0 | 5 | 5 | 4 | 5 | 5 |
| 60 | 125 | 0 | 3 | 5 | 0 | 4 | 4 |
| | 250 | 0 | 4 | 5 | 0 | 4 | 4 |
| | 500 | 0 | 4 | 5 | 1 | 5 | 5 |
| | 1000 | 0 | 5 | 5 | 2 | 5 | 5 |
| 61 | 125 | 0 | 5 | 5 | 0 | 5 | 5 |
| | 250 | 0 | 5 | 5 | 1 | 5 | 5 |
| | 500 | 0 | 5 | 5 | 2 | 5 | 5 |
| | 1000 | 0 | 5 | 5 | 3 | 5 | 5 |
| 62 | 125 | 0 | 5 | 5 | 3 | 5 | 5 |
| | 250 | 0 | 5 | 5 | 4 | 5 | 5 |
| | 500 | 0 | 5 | 5 | 4 | 5 | 5 |
| | 1000 | 0 | 5 | 5 | 5 | 5 | 5 |
| 63 | 125 | 0 | 5 | 5 | 1 | 4 | 4 |
| | 250 | 0 | 5 | 5 | 1 | 5 | 5 |
| | 500 | 0 | 5 | 5 | 2 | 5 | 5 |
| | 1000 | 0 | 5 | 5 | 2 | 5 | 5 |
| 64 | 125 | 0 | 5 | 5 | 1 | 5 | 5 |
| | 250 | 0 | 5 | 5 | 1 | 5 | 5 |
| | 500 | 0 | 5 | 5 | 2 | 5 | 5 |
| | 1000 | 0 | 5 | 5 | 3 | 5 | 5 |
| 65 | 125 | 0 | 5 | 5 | 2 | 5 | 5 |
| | 250 | 0 | 5 | 5 | 2 | 5 | 5 |
| | 500 | 0 | 5 | 5 | 3 | 5 | 5 |
| | 1000 | 0 | 5 | 5 | 4 | 5 | 5 |
| 67 | 125 | 0 | 5 | 5 | 1 | 4 | 4 |
| | 250 | 0 | 5 | 5 | 1 | 5 | 5 |
| | 500 | 0 | 5 | 5 | 2 | 5 | 5 |
| | 1000 | 0 | 5 | 5 | 3 | 5 | 5 |
| 68 | 125 | 0 | 5 | 5 | 3 | 3 | 3 |
| | 250 | 0 | 5 | 5 | 4 | 5 | 5 |
| | 500 | 0 | 5 | 5 | 5 | 5 | 5 |
| | 1000 | 0 | 5 | 5 | 5 | 5 | 5 |
| 69 | 125 | 0 | 5 | 5 | 1 | 5 | 5 |
| | 250 | 0 | 5 | 5 | 1 | 5 | 5 |
| | 500 | 0 | 5 | 5 | 2 | 5 | 5 |
| | 1000 | 0 | 5 | 5 | 3 | 5 | 5 |
| 70 | 125 | 0 | 5 | 5 | 1 | 1 | 1 |
| | 250 | 0 | 5 | 5 | 1 | 2 | 2 |
| | 500 | 0 | 5 | 5 | 1 | 4 | 4 |
| | 1000 | 0 | 5 | 5 | 2 | 5 | 5 |
| 71 | 125 | 0 | 5 | 5 | 1 | 5 | 5 |
| | 250 | 0 | 5 | 5 | 3 | 5 | 5 |
| | 500 | 0 | 5 | 5 | 3 | 5 | 5 |
| | 1000 | 0 | 5 | 5 | 4 | 5 | 5 |
| 75 | 125 | 0 | 5 | 5 | 3 | 5 | 5 |
| | 250 | 0 | 5 | 5 | 3 | 5 | 5 |
| | 500 | 0 | 5 | 5 | 4 | 5 | 5 |
| | 1000 | 0 | 5 | 5 | 4 | 5 | 5 |
| 81 | 125 | 0 | 5 | 5 | 1 | 5 | 5 |
| | 250 | 0 | 5 | 5 | 2 | 5 | 5 |
| | 500 | 0 | 5 | 5 | 2 | 5 | 5 |
| | 1000 | 0 | 5 | 5 | 3 | 5 | 5 |
| 83 | 125 | 0 | 5 | 5 | 1 | 5 | 5 |
| | 250 | 0 | 5 | 5 | 2 | 5 | 5 |
| | 500 | 0 | 5 | 5 | 3 | 5 | 5 |
| | 1000 | 0 | 5 | 5 | 4 | 5 | 5 |
| 86 | 125 | 0 | 5 | 5 | 3 | 5 | 5 |
| | 250 | 0 | 5 | 5 | 4 | 5 | 5 |
| | 500 | 0 | 5 | 5 | 5 | 5 | 5 |
| | 1000 | 0 | 5 | 5 | 5 | 5 | 5 |
| 87 | 125 | 0 | 5 | 5 | 3 | 5 | 5 |
| | 250 | 0 | 5 | 5 | 3 | 5 | 5 |

TABLE 1-continued

| Compound No. | Dose (g/10 ares) | Phytotoxicity against rice plant | Herbicidal effects | | | | |
|---|---|---|---|---|---|---|---|
| | | | Barnyard grass | Umbrella plant | Bulrush | Monochoria | Tooth cup |
| | 500 | 0 | 5 | 5 | 4 | 5 | 5 |
| | 1000 | 0 | 5 | 5 | 4 | 5 | 5 |
| 89 | 125 | 0 | 5 | 5 | 4 | 5 | 5 |
| | 250 | 0 | 5 | 5 | 5 | 5 | 5 |
| | 500 | 0 | 5 | 5 | 5 | 5 | 5 |
| | 1000 | 0 | 5 | 5 | 5 | 5 | 5 |
| 90 | 125 | 0 | 4 | 5 | 1 | 4 | 4 |
| | 250 | 0 | 5 | 5 | 2 | 5 | 5 |
| | 500 | 0 | 5 | 5 | 2 | 5 | 5 |
| | 1000 | 0 | 5 | 5 | 3 | 5 | 5 |
| 92 | 125 | 0 | 5 | 5 | 5 | 5 | 5 |
| | 250 | 0 | 5 | 5 | 5 | 5 | 5 |
| | 500 | 0 | 5 | 5 | 5 | 5 | 5 |
| | 1000 | 0 | 5 | 5 | 5 | 5 | 5 |
| 93 | 125 | 0 | 5 | 5 | 5 | 5 | 5 |
| | 250 | 0 | 5 | 5 | 5 | 5 | 5 |
| | 500 | 0 | 5 | 5 | 5 | 5 | 5 |
| | 1000 | 0 | 5 | 5 | 5 | 5 | 5 |
| 94 | 125 | 0 | 4 | 5 | 1 | 3 | 3 |
| | 250 | 0 | 5 | 5 | 1 | 4 | 4 |
| | 500 | 0 | 5 | 5 | 2 | 5 | 5 |
| | 1000 | 0 | 5 | 5 | 2 | 5 | 5 |
| 97 | 125 | 0 | 5 | 5 | 4 | 5 | 5 |
| | 250 | 0 | 5 | 5 | 5 | 5 | 5 |
| | 500 | 0 | 5 | 5 | 5 | 5 | 5 |
| | 1000 | 0 | 5 | 5 | 5 | 5 | 5 |
| 98 | 125 | 0 | 5 | 5 | 5 | 5 | 5 |
| | 250 | 0 | 5 | 5 | 5 | 5 | 5 |
| | 500 | 0 | 5 | 5 | 5 | 5 | 5 |
| | 1000 | 0 | 5 | 5 | 5 | 5 | 5 |
| 101 | 125 | 0 | 5 | 5 | 0 | 5 | 5 |
| | 250 | 0 | 5 | 5 | 0 | 5 | 5 |
| | 500 | 0 | 5 | 5 | 1 | 5 | 5 |
| | 1000 | 0 | 5 | 5 | 1 | 5 | 5 |
| 105 | 125 | 0 | 5 | 5 | 0 | 4 | 5 |
| | 250 | 0 | 5 | 5 | 1 | 5 | 5 |
| | 500 | 0 | 5 | 5 | 1 | 5 | 5 |
| | 1000 | 0 | 5 | 5 | 2 | 5 | 5 |
| 106 | 125 | 0 | 5 | 5 | 0 | 5 | 5 |
| | 250 | 0 | 5 | 5 | 1 | 5 | 5 |
| | 500 | 0 | 5 | 5 | 1 | 5 | 5 |
| | 1000 | 0 | 5 | 5 | 2 | 5 | 5 |
| 107 | 125 | 0 | 5 | 5 | 1 | 5 | 5 |
| | 250 | 0 | 5 | 5 | 2 | 5 | 5 |
| | 500 | 0 | 5 | 5 | 2 | 5 | 5 |
| | 1000 | 0 | 5 | 5 | 3 | 5 | 5 |
| 109 | 125 | 0 | 5 | 5 | 1 | 5 | 5 |
| | 250 | 0 | 5 | 5 | 2 | 5 | 5 |
| | 500 | 0 | 5 | 5 | 3 | 5 | 5 |
| | 1000 | 0 | 5 | 5 | 3 | 5 | 5 |
| 113 | 125 | 0 | 5 | 5 | 4 | 5 | 5 |
| | 250 | 0 | 5 | 5 | 4 | 5 | 5 |
| | 500 | 0 | 5 | 5 | 5 | 5 | 5 |
| | 1000 | 0 | 5 | 5 | 5 | 5 | 5 |
| 115 | 125 | 0 | 5 | 5 | 3 | 4 | 3 |
| | 250 | 0 | 5 | 5 | 3 | 5 | 4 |
| | 500 | 0 | 5 | 5 | 5 | 5 | 5 |
| | 1000 | 0 | 5 | 5 | 5 | 5 | 5 |
| 116 | 125 | 0 | 5 | 5 | 4 | 4 | 5 |
| | 250 | 0 | 5 | 5 | 5 | 5 | 5 |
| | 500 | 0 | 5 | 5 | 5 | 5 | 5 |
| | 1000 | 0 | 5 | 5 | 5 | 5 | 5 |
| 119 | 125 | 0 | 5 | 5 | 3 | 4 | 4 |
| | 250 | 0 | 5 | 5 | 3 | 4 | 5 |
| | 500 | 0 | 5 | 5 | 4 | 4 | 5 |
| | 1000 | 0 | 5 | 5 | 4 | 5 | 5 |
| 123 | 125 | 0 | 5 | 5 | 0 | 4 | 5 |
| | 250 | 0 | 5 | 5 | 0 | 4 | 5 |
| | 500 | 0 | 5 | 5 | 1 | 5 | 5 |
| | 1000 | 0 | 5 | 5 | 1 | 5 | 5 |
| 124 | 125 | 0 | 5 | 5 | 5 | 5 | 5 |
| | 250 | 0 | 5 | 5 | 5 | 5 | 5 |
| | 500 | 0 | 5 | 5 | 5 | 5 | 5 |
| | 1000 | 0 | 5 | 5 | 5 | 5 | 5 |
| 125 | 125 | 0 | 2 | 3 | 2 | 3 | 3 |
| | 250 | 0 | 3 | 5 | 3 | 4 | 3 |
| | 500 | 0 | 3 | 5 | 3 | 4 | 4 |
| | 1000 | 0 | 4 | 5 | 4 | 5 | 4 |
| 126 | 125 | 0 | 3 | 5 | 0 | 3 | 2 |

TABLE 1-continued

| Compound No. | Dose (g/10 ares) | Phytotoxicity against rice plant | Herbicidal effects ||||| 
| | | | Barnyard grass | Umbrella plant | Bulrush | Monochoria | Tooth cup |
|---|---|---|---|---|---|---|---|
| | 250 | 0 | 4 | 5 | 1 | 4 | 3 |
| | 500 | 0 | 4 | 5 | 1 | 4 | 4 |
| | 1000 | 0 | 4 | 5 | 2 | 5 | 4 |
| 129 | 125 | 0 | 5 | 5 | 0 | 3 | 2 |
| | 250 | 0 | 5 | 5 | 0 | 3 | 3 |
| | 500 | 0 | 5 | 5 | 1 | 4 | 3 |
| | 1000 | 0 | 5 | 5 | 2 | 4 | 4 |
| 131 | 125 | 0 | 4 | 5 | 0 | 4 | 1 |
| | 250 | 0 | 5 | 5 | 0 | 4 | 2 |
| | 500 | 0 | 5 | 5 | 1 | 4 | 2 |
| | 1000 | 0 | 5 | 5 | 1 | 5 | 3 |
| 133 | 125 | 0 | 1 | 4 | 0 | 1 | 0 |
| | 250 | 0 | 2 | 4 | 0 | 2 | 1 |
| | 500 | 0 | 2 | 5 | 1 | 3 | 1 |
| | 1000 | 0 | 3 | 5 | 1 | 3 | 2 |
| 134 | 125 | 0 | 1 | 3 | 0 | 0 | 0 |
| | 250 | 0 | 2 | 4 | 0 | 0 | 1 |
| | 500 | 0 | 3 | 5 | 1 | 1 | 1 |
| | 1000 | 0 | 4 | 5 | 2 | 2 | 3 |
| 135 | 125 | 0 | 5 | 5 | 4 | 4 | 3 |
| | 250 | 0 | 5 | 5 | 4 | 5 | 4 |
| | 500 | 0 | 5 | 5 | 5 | 5 | 4 |
| | 1000 | 0 | 5 | 5 | 5 | 5 | 5 |
| 136 | 125 | 0 | 2 | 5 | 2 | 2 | 2 |
| | 250 | 0 | 3 | 5 | 2 | 3 | 3 |
| | 500 | 0 | 4 | 5 | 3 | 3 | 3 |
| | 1000 | 0 | 5 | 5 | 4 | 4 | 4 |
| 137 | 125 | 0 | 5 | 5 | 3 | 5 | 5 |
| | 250 | 0 | 5 | 5 | 4 | 5 | 5 |
| | 500 | 0 | 5 | 5 | 4 | 5 | 5 |
| | 1000 | 0 | 5 | 5 | 4.5 | 5 | 5 |
| 140 | 125 | 0 | 5 | 5 | 3 | 5 | 4 |
| | 250 | 0 | 5 | 5 | 3 | 5 | 4 |
| | 500 | 0 | 5 | 5 | 4 | 5 | 5 |
| | 1000 | 0 | 5 | 5 | 4 | 5 | 5 |
| 144 | 125 | 0 | 5 | 5 | 3 | 5 | 4 |
| | 250 | 0 | 5 | 5 | 3 | 5 | 4 |
| | 500 | 0 | 5 | 5 | 4 | 5 | 4.5 |
| | 1000 | 0 | 5 | 5 | 4 | 5 | 5 |
| 148 | 125 | 0 | 5 | 5 | 1 | 5 | 2 |
| | 250 | 0 | 5 | 5 | 2 | 5 | 3 |
| | 500 | 0 | 5 | 5 | 2 | 5 | 4 |
| | 1000 | 0 | 5 | 5 | 3 | 5 | 4 |
| 149 | 125 | 0 | 5 | 5 | 3 | 5 | 5 |
| | 250 | 0 | 5 | 5 | 4 | 5 | 5 |
| | 500 | 0 | 5 | 5 | 4 | 5 | 5 |
| | 1000 | 0 | 5 | 5 | 4.5 | 5 | 5 |
| 152 | 125 | 0 | 5 | 5 | 2 | 5 | 4 |
| | 250 | 0 | 5 | 5 | 2 | 5 | 4 |
| | 500 | 0 | 5 | 5 | 3 | 5 | 5 |
| | 1000 | 0 | 5 | 5 | 3 | 5 | 5 |
| 154 | 125 | 0 | 5 | 5 | 3 | 3 | 5 |
| | 250 | 0 | 5 | 5 | 3 | 3 | 5 |
| | 500 | 0 | 5 | 5 | 4 | 4 | 5 |
| | 1000 | 0 | 5 | 5 | 4 | 4 | 5 |
| 155 | 125 | 0 | 5 | 5 | 4 | 5 | 5 |
| | 250 | 0 | 5 | 5 | 4 | 5 | 5 |
| | 500 | 0 | 5 | 5 | 5 | 5 | 5 |
| | 1000 | 0 | 5 | 5 | 5 | 5 | 5 |
| 156 | 125 | 0 | 5 | 5 | 4 | 5 | 4 |
| | 250 | 0 | 5 | 5 | 5 | 5 | 5 |
| | 500 | 0 | 5 | 5 | 5 | 5 | 5 |
| | 1000 | 0 | 5 | 5 | 5 | 5 | 5 |
| 157 | 125 | 0 | 4 | 5 | 0 | 3 | 4 |
| | 250 | 0 | 5 | 5 | 0 | 4 | 5 |
| | 500 | 0 | 5 | 5 | 1 | 4 | 5 |
| | 1000 | 0 | 5 | 5 | 1 | 5 | 5 |
| 158 | 125 | 0 | 5 | 5 | 4 | 5 | 5 |
| | 250 | 0 | 5 | 5 | 4 | 5 | 5 |
| | 500 | 0 | 5 | 5 | 5 | 5 | 5 |
| | 1000 | 0 | 5 | 5 | 5 | 5 | 5 |
| 160 | 125 | 0 | 1 | 3 | 1 | 2 | 2 |
| | 250 | 0 | 2 | 4 | 2 | 3 | 3 |
| | 500 | 0 | 3 | 5 | 3 | 5 | 4 |
| | 1000 | 0 | 4 | 5 | 4 | 5 | 5 |
| 161 | 125 | 0 | 3 | 3 | 2 | 3 | 1 |
| | 250 | 0 | 4 | 4 | 2 | 4 | 2 |
| | 500 | 0 | 4 | 5 | 3 | 5 | 3 |
| | 1000 | 0 | 5 | 5 | 3 | 5 | 4 |

TABLE 1-continued

| Compound No. | Dose (g/10 ares) | Phytotoxicity against rice plant | Herbicidal effects |||||
|---|---|---|---|---|---|---|---|
| | | | Barnyard grass | Umbrella plant | Bulrush | Monochoria | Tooth cup |
| 163 | 125 | 0 | 5 | 5 | 4 | 5 | 4 |
| | 250 | 0 | 5 | 5 | 4 | 5 | 5 |
| | 500 | 0 | 5 | 5 | 4 | 5 | 5 |
| | 1000 | 0 | 5 | 5 | 4 | 5 | 5 |
| 165 | 125 | 0 | 5 | 5 | 2 | 5 | 4 |
| | 250 | 0 | 5 | 5 | 3 | 5 | 4 |
| | 500 | 0 | 5 | 5 | 3 | 5 | 5 |
| | 1000 | 0 | 5 | 5 | 4 | 5 | 5 |
| 167 | 125 | 0 | 5 | 5 | 3 | 5 | 4 |
| | 250 | 0 | 5 | 5 | 3 | 5 | 5 |
| | 500 | 0 | 5 | 5 | 4 | 5 | 5 |
| | 1000 | 0 | 5 | 5 | 4 | 5 | 5 |
| 170 | 125 | 0 | 5 | 5 | 3 | 5 | 4 |
| | 250 | 0 | 5 | 5 | 4 | 5 | 4 |
| | 500 | 0 | 5 | 5 | 4 | 5 | 5 |
| | 1000 | 0 | 5 | 5 | 4 | 5 | 5 |
| 171 | 125 | 0 | 5 | 5 | 3 | 5 | 4 |
| | 250 | 0 | 5 | 5 | 4 | 5 | 4 |
| | 500 | 0 | 5 | 5 | 5 | 5 | 5 |
| | 1000 | 0 | 5 | 5 | 5 | 5 | 5 |
| 172 | 125 | 0 | 5 | 5 | 4 | 5 | 4 |
| | 250 | 0 | 5 | 5 | 4 | 5 | 4 |
| | 500 | 0 | 5 | 5 | 5 | 5 | 5 |
| | 1000 | 0 | 5 | 5 | 5 | 5 | 5 |
| 173 | 125 | 0 | 5 | 5 | 4 | 5 | 4 |
| | 250 | 0 | 5 | 5 | 4 | 5 | 5 |
| | 500 | 0 | 5 | 5 | 5 | 5 | 5 |
| | 1000 | 0 | 5 | 5 | 5 | 5 | 5 |
| 174 | 125 | 0 | 5 | 5 | 3 | 5 | 3 |
| | 250 | 0 | 5 | 5 | 3 | 5 | 3 |
| | 500 | 0 | 5 | 5 | 4 | 5 | 3 |
| | 1000 | 0 | 5 | 5 | 5 | 5 | 4 |
| Benthiocarb (Reference agent) | 125 | 1 | 5 | 5 | 2 | 2 | 3 |
| | 250 | 2 | 5 | 5 | 2 | 2 | 3 |
| | 500 | 2 | 5 | 5 | 3 | 3 | 4 |
| | 1000 | 3 | 5 | 5 | 5 | 4 | 5 |
| Not treated | 0 | 0 | 0 | 0 | 0 | 0 | 0 |

EXAMPLE 5

[Test for the Herbicidal Effects Under Submerged Conditions (2)]

Paddy field soil was changed in porcelain pots having a diameter of 9 cm, and then water was added. After the soil was tilled, seeds of barnyard grass were sown on the surface of the soil and two bunches of rice plants (variety: Nihonbare) being in 2-leaf stage were transplanted in 1 cm depth. The pots were flooded to give water depth of 2 cm on the next day and predetermined amount of water dispersible powder of the herbicides of the present invention, which was dispersed in 10 ml of water, was added dropwise onto the surface of water in every pots for the treatment before the germination of and at the time of both 1.2- and 2-leaf stages of barnyard grass. The pots were settled in a greenhouse and received water in proper time intervals. The examination was carried out after 3 weeks from the treatment with the chemicals and the results were evaluated in the similar manner as in Example 4. The results are shown in Table 2.

TABLE 2

| Compound No. | Dose (g/10 ares) | Phytotoxicity against rice plant | Herbicidal effects against barnyard grass |||
|---|---|---|---|---|---|
| | | | Pre-emergence | 1.2-Leaf stage | 2-Leaf stage |
| 1 | 12.5 | 0 | 5 | — | 5 |
| | 25 | 0 | 5 | — | 5 |
| | 50 | 0 | 5 | — | 5 |
| | 100 | 0 | 5 | — | 5 |
| 3 | 12.5 | 0 | 5 | — | 5 |
| | 25 | 0 | 5 | — | 5 |
| | 50 | 0 | 5 | — | 5 |
| | 100 | 0 | 5 | — | 5 |
| 35 | 12.5 | 0 | 5 | — | 5 |
| | 25 | 0 | 5 | — | 5 |
| | 50 | 0 | 5 | — | 5 |
| | 100 | 0 | 5 | — | 5 |
| 44 | 12.5 | 0 | 5 | — | 4 |
| | 25 | 0 | 5 | — | 5 |
| | 50 | 0 | 5 | — | 5 |
| | 100 | 0 | 5 | — | 5 |
| 62 | 12.5 | 0 | 5 | 5 | — |
| | 25 | 0 | 5 | 5 | — |
| | 50 | 0 | 5 | 5 | — |

TABLE 2-continued

| Compound No. | Dose (g/10 ares) | Phytotoxicity against rice plant | Herbicidal effects against barnyard grass | | |
|---|---|---|---|---|---|
| | | | Pre-emergence | 1.2-Leaf stage | 2-Leaf stage |
| | 100 | 0 | 5 | 5 | — |
| 69 | 12.5 | 0 | 5 | 4 | — |
| | 25 | 0 | 5 | 4 | — |
| | 50 | 0 | 5 | 5 | — |
| | 100 | 0 | 5 | 5 | — |
| 72 | 12.5 | 0 | 5 | 5 | — |
| | 25 | 0 | 5 | 5 | — |
| | 50 | 0 | 5 | 5 | — |
| | 100 | 0 | 5 | 5 | — |
| 106 | 12.5 | 0 | 5 | — | — |
| | 25 | 0 | 5 | — | — |
| | 50 | 0 | 5 | — | — |
| | 100 | 0 | 5 | — | — |
| 116 | 12.5 | 0 | 5 | — | — |
| | 25 | 0 | 5 | — | — |
| | 50 | 0 | 5 | — | — |
| | 100 | 0 | 5 | — | — |
| 124 | 12.5 | 0 | 5 | — | — |
| | 25 | 0 | 5 | — | — |
| | 50 | 0 | 5 | — | — |
| | 100 | 0 | 5 | — | — |
| 137 | 12.5 | 0 | 3 | — | — |
| | 25 | 0 | 5 | — | — |
| | 50 | 0 | 5 | — | — |
| | 100 | 0 | 5 | — | — |
| 152 | 12.5 | 0 | 5 | — | — |
| | 25 | 0 | 5 | — | — |
| | 50 | 0 | 5 | — | — |
| | 100 | 0 | 5 | — | — |
| Benthiocarb (Reference agent) | 12.5 | 0 | 2 | 1 | 1 |
| | 25 | 0 | 3 | 2 | 2 |
| | 50 | 0 | 4 | 2.5 | 2.5 |
| | 100 | 1 | 5 | 4 | 4 |
| Not treated | 0 | 0 | 0 | 0 | 0 |

EXAMPLE 6

[Test for the Herbicidal Effects by the Surface Treatment of Farmland Soil]

Farmland soil was charged into porcelain pots having a diameter of 12 cm and several kinds of crop seeds together with weed seeds were sown. The seeds were further covered by the soil in 1 cm thickness. Predetermined amount of water dispersible powder of the herbicides of the present invention, which was dispersed in 10 ml of water per every pots, was sprayed on the surface of soil for the treatment. The pots were stationarily placed in a greenhouse and received sprayed water in proper time intervals. After 3 weeks from the treatment with the chemicals, the herbicidal effects and the influences against soybean and cotton plants were examined in the similar manner as in Example 4. The results are shown in Table 3.

TABLE 3

| Compound No. | Dose (g/10 ares) | Phytotoxicity | | Herbicidal effects | | |
|---|---|---|---|---|---|---|
| | | Soybean plant | Cotton plant | Barnyard grass | Crab grass | Foxtail |
| 1 | 100 | 0 | 0 | 5 | 5 | 5 |
| | 200 | 0 | 0 | 5 | 5 | 5 |
| | 400 | 0 | 0 | 5 | 5 | 5 |
| | 800 | 0 | 0 | 5 | 5 | 5 |
| 3 | 100 | 0 | 0 | 5 | 5 | 5 |
| | 200 | 0 | 0 | 5 | 5 | 5 |
| | 400 | 0 | 0 | 5 | 5 | 5 |
| | 800 | 0 | 0 | 5 | 5 | 5 |
| 35 | 100 | 0 | 0 | 5 | 5 | 5 |
| | 200 | 0 | 0 | 5 | 5 | 5 |
| | 400 | 0 | 0 | 5 | 5 | 5 |
| | 800 | 0 | 0 | 5 | 5 | 5 |
| 44 | 100 | 0 | 0 | 5 | 5 | 5 |
| | 200 | 0 | 0 | 5 | 5 | 5 |
| | 400 | 0 | 0 | 5 | 5 | 5 |
| | 800 | 0 | 0 | 5 | 5 | 5 |
| 62 | 50 | 0 | 0 | 5 | 5 | 5 |
| | 100 | 0 | 0 | 5 | 5 | 5 |
| | 200 | 0 | 0 | 5 | 5 | 5 |
| | 400 | 0 | 0 | 5 | 5 | 5 |
| 69 | 50 | 0 | 0 | 4 | 4 | 4 |
| | 100 | 0 | 0 | 4 | 5 | 4.5 |
| | 200 | 0 | 0 | 5 | 5 | 5 |
| | 400 | 0 | 0 | 5 | 5 | 5 |
| 72 | 50 | 0 | 0 | 5 | 5 | 5 |

TABLE 3-continued

| Compound No. | Dose (g/10 ares) | Phytotoxicity | | Herbicidal effects | | |
|---|---|---|---|---|---|---|
| | | Soybean plant | Cotton plant | Barnyard grass | Crab grass | Foxtail |
| | 100 | 0 | 0 | 5 | 5 | 5 |
| | 200 | 0 | 0 | 5 | 5 | 5 |
| | 400 | 0 | 0 | 5 | 5 | 5 |
| 98 | 50 | 0 | 0 | 5 | 5 | 5 |
| | 100 | 0 | 0 | 5 | 5 | 5 |
| | 200 | 0 | 0 | 5 | 5 | 5 |
| | 400 | 0 | 0 | 5 | 5 | 5 |
| 116 | 50 | 0 | 0 | 5 | 5 | 5 |
| | 100 | 0 | 0 | 5 | 5 | 5 |
| | 200 | 0 | 0 | 5 | 5 | 5 |
| | 400 | 0 | 0 | 5 | 5 | 5 |
| 124 | 50 | 0 | 0 | 5 | 5 | 5 |
| | 100 | 0 | 0 | 5 | 5 | 5 |
| | 200 | 0 | 0 | 5 | 5 | 5 |
| | 400 | 0 | 0 | 5 | 5 | 5 |
| 137 | 50 | 0 | 0 | 3 | 4 | 3 |
| | 100 | 0 | 0 | 4 | 5 | 4 |
| | 200 | 0 | 0 | 5 | 5 | 5 |
| | 400 | 0 | 0 | 5 | 5 | 5 |
| 152 | 50 | 0 | 0 | 5 | 5 | 5 |
| | 100 | 0 | 0 | 5 | 5 | 5 |
| | 200 | 0 | 0 | 5 | 5 | 5 |
| | 400 | 0 | 0 | 5 | 5 | 5 |
| Benthiocarb (Reference agent) | 50 | 0 | 0 | 3 | 4 | 3 |
| | 100 | 0 | 0 | 4 | 5 | 4 |
| | 200 | 0 | 0 | 5 | 5 | 5 |
| | 400 | 0 | 0 | 5 | 5 | 5 |
| | 800 | 0 | 0 | 5 | 5 | 5 |
| Not treated | | 0 | 0 | 0 | 0 | 0 |

What is claimed is:

1. A method for the control of weeds, comprising the application of a herbicidal composition containing a thiocarbamate derivative represented by the general formula (I) as an active ingredient incorporated in an inert carrier to the locus to be protected

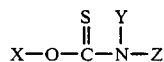

wherein
X is 5-indanyl, 5,6,7,8-tetrahydro-2-naphthyl, 1,4-methano-1,2,3,4-tetrahydro-6-naphthyl, 1,4-ethano-1,2,3,4-tetrahydro-6-naphthyl, or substituted phenyl having one or two of the same or different substituents selected from the group consisting of halogeno, lower alkyl, lower alkoxy, lower alkenyloxy, lower alkynyloxy, lower alkylthio, acyl, nitro, cyano, methylenedioxy, and trifluoromethyl,
Y is lower alkyl,
Z is naphthyl which is unsubstituted or phenyl which is unsubstituted or substituted by one or two of the same or different substituents selected from the group consisting of halogeno, lower alkyl, lower alkoxy, lower alkylamino, trifluoromethyl, and fluorinated lower alkoxy.

2. A method for the control of weeds, comprising the application of a herbicidal composition containing a thiocarbamate derivative according to claim 1, wherein
X is 5-indanyl, 5,6,7,8-tetrahydro-2-naphthyl, 1,4-methano-1,2,3,4-tetrahydro-6-naphthyl, 1,4-ethano-1,2,3,4-tetrahydro-6-naphthyl, or substituted phenyl having one or two of the same or different substituents selected from the group consisting of a chlorine atom, a bromine atom, alkyl of 1 to 5 carbon atoms, alkoxy of 1 to 4 carbon atoms, alkenyloxy of 3 carbon atoms, alkynyloxy of 3 carbon atoms, methylthio, acetyl, nitro, cyano, methylenedioxy, and trifluoromethyl.

3. A method for the control of weeds, comprising the application of a herbicidal composition containing a thiocarbamate derivative according to claim 1, wherein
Y is alkyl of 1 to 2 carbon atoms.

4. A method for the control of weeds, comprising the application of a herbicidal composition containing a thiocarbamate derivative according to claim 1, wherein
Z is naphthyl which is unsubstituted or or phenyl which is unsubstituted or substituted by one or two of the same or different substituents selected from the group consisting of a chlorine atom, a bromine atom, a fluorine atom, alkyl of 1 to 2 carbon atoms, methoxy, dimethylamino, trifluoromethyl, and fluorinated alkoxy of 1 to 2 carbon atoms.

5. A method for the control of weeds, comprising the application of a herbicidal composition containing a thiocarbamate derivative according to claim 1, wherein
X is 5-indanyl, 5,6,7,8-tetrahydro-2-naphthyl, 1,4-methano-1,2,3,4-tetrahydro-6-naphthyl, 1,4-ethano-1,2,3,4-tetrahydro-6-naphthyl, or substituted phenyl having one or two of the same or different substituents selected from the group consisting of a chlorine atom, a bromine atom, alkyl of 1 to 4 carbon atoms, alkoxy of 1 to 4 carbon atoms, alkenyloxy of 3 carbon atoms, alkynyloxy of 3 carbon atoms, methylthio, acetyl, nitro, cyano, methylenedioxy, and trifluoromethyl,
Y is alkyl of 1 to 2 carbon atoms,
Z is naphthyl which is unsubstituted or phenyl which is unsubstituted or substituted by one or two of the same or different substituents selected from the group consisting of a chlorine atom, a bromine atom, a fluorine atom, alkyl of 1 to 2 carbon atoms, methoxy, dimethylamino, trifluoromethyl, and fluorinated alkoxy of 1 to 2 carbon atoms.

* * * * *